United States Patent
Eilebrecht et al.

(10) Patent No.: US 9,468,390 B2
(45) Date of Patent: Oct. 18, 2016

(54) CONTACTLESS ELECTROCARDIOGRAPHIC MEASUREMENT SENSOR

(71) Applicant: FORD GLOBAL TECHNOLOGIES, LLC, Dearborn, MI (US)

(72) Inventors: Benjamin Eilebrecht, Herne NRW (DE); Jeroen Lem, Maastricht (NL); Marcel Mathissen, Wuerselen NRW (DE); Achim Lindner, Euskirchen (DE); Rainer Vogt, Aachen NRW (DE); Marian Walter, Aachen (DE); Steffen Leonhardt, Aachen (DE)

(73) Assignee: Ford Global Technologies, LLC, Dearborn, MI (US)

( * ) Notice: Subject to any disclaimer, the term of this patent is extended or adjusted under 35 U.S.C. 154(b) by 97 days.

(21) Appl. No.: 14/497,434

(22) Filed: Sep. 26, 2014

(65) Prior Publication Data

US 2015/0094603 A1   Apr. 2, 2015

(30) Foreign Application Priority Data

Sep. 27, 2013   (DE) .......... 10 2013 219 513

(51) Int. Cl.
| | |
|---|---|
| *A61B 5/0408* | (2006.01) |
| *A61B 5/00* | (2006.01) |
| *A61B 5/0428* | (2006.01) |
| *A61B 5/18* | (2006.01) |

(52) U.S. Cl.
CPC .......... *A61B 5/04288* (2013.01); *A61B 5/0408* (2013.01); *A61B 5/18* (2013.01); *A61B 5/6893* (2013.01); *A61B 2562/046* (2013.01)

(58) Field of Classification Search
CPC .. A61B 5/04; A61B 5/04012; A61B 5/0402; A61B 5/0408; A61B 5/0428; A61B 5/04284; A61B 5/04288; A61B 5/18; A61B 5/6887; A61B 5/6891; A61B 5/6892; A61B 5/6893; A61B 2562/046
USPC ........................................ 600/382, 393, 509
See application file for complete search history.

(56) References Cited

U.S. PATENT DOCUMENTS

| | | | |
|---|---|---|---|
| 4,476,871 A * | 10/1984 | Hon .................. | A61B 5/035 200/81.4 |
| 7,684,854 B2 | 3/2010 | Park et al. | |
| 2014/0275888 A1* | 9/2014 | Wegerich .......... | A61B 5/6831 600/324 |

FOREIGN PATENT DOCUMENTS

| | | |
|---|---|---|
| DE | 102008049112 A1 | 5/2009 |
| DE | 202012001096 U1 | 3/2012 |
| EP | 2532306 A1 | 12/2012 |
| FR | 2979029 A1 | 2/2013 |

OTHER PUBLICATIONS

European Patent Office, Search Report for the corresponding European Patent Application No. EP 14 18 6656 dated Jan. 28, 2015.

* cited by examiner

*Primary Examiner* — Allen Porter, Jr.
(74) *Attorney, Agent, or Firm* — Frank A. MacKenzie; Brooks Kushman P.C.

(57) ABSTRACT

A sensor for contactless electrocardiographic measurement of a person has at least one electrically conductive, planar electrode having a measurement surface facing the person and a connection surface facing away from the person. An electrical terminal for connection with a measurement apparatus is spaced from the connection surface such that the connection surface is only placed in electrical connection with the terminal when pressure of a required magnitude is applied to the measurement. The electrical connection may be achieved by a switching contact disposed between the electrode and the terminal which is brought into contact with both the electrode and the terminal when the electrode is deflected toward the terminal by the pressure. A compressible material is disposed between the electrode and the terminal to allow tuning of the pressure required to achieve electrical contact.

15 Claims, 4 Drawing Sheets

CONTACTLESS ELECTROCARDIOGRAPHIC MEASUREMENT SENSOR

CROSS-REFERENCE TO RELATED APPLICATIONS

This application claims foreign priority benefits under 35 U.S.C. §119(a)-(d) to DE 10 2013 219 513.3 filed Sep. 27, 2013, which is hereby incorporated by reference in its entirety

TECHNICAL FIELD

The present invention relates to contactless electrocardiographic measurement of a subject seated in a motor vehicle, and more specifically to a contactless electrocardiographic sensor having a pressure-responsive feature to improve signal quality and reliability.

BACKGROUND

Measurement of the electrical potential, or electrical field strength, on the skin of a person by means of electrocardiographic sensors forms the basis of many medical diagnostic methods. In this way, for example, an electrocardiogram (ECG) may be recorded or the heart rate may be determined from the measured electrical potentials.

In conventional measurement methods for measuring the electrical potential on the skin, the latter is acquired by electrodes which are in direct electrical contact with the surface of the skin. An electrically conductive connection is thus established between the skin, on the one hand, and the electrode, on the other hand. In this case, however, it often proves difficult to ensure a sufficiently good electrical contact between the electrode and the skin, and therefore the body of the person being examined (the subject). Furthermore, the use of such diagnostic methods is also increasingly being provided in application fields in which direct access to the skin of the subject is not available, for example in vehicle applications for monitoring body functions and/or vital parameters of vehicle passengers on seats or bunks.

For example, U.S. Pat. No. 7,684,854 B2 discloses a sensor for contactless electrocardiographic measurement on a person. The person may in this case be on a stool, in a bed or on a vehicle seat. The electrocardiogram can be recorded from the body of the person wearing clothing without direct contact with the skin. The sensor comprises a flat electrically conductive electrode which comprises a measurement surface facing toward the person and a connection surface which faces away from the person, lies opposite the measurement surface and is electrically connected to a preamplifier. The electrode and the preamplifier of the sensor are enclosed by shielding.

Another contactless sensor for recording an electrocardiogram of a person is disclosed by EP 2 532 306 A1. The sensor comprises an electrically conductive electrode and a detection device, which is electrically connected to the electrode and is configured in order to amplify the signals received by the electrode. The sensor is intended to be arranged in a vehicle seat and to determine particular physiological parameters of a driver sitting on the vehicle seat.

DE 20 2012 001 096 U1 discloses capacitive sensors for capacitive recording of vital parameters of a driver of a vehicle. To this end, the sensors are fitted in or on the backrest of the seat of the vehicle. In particular, according to one embodiment it is proposed to arrange the sensors in or on the backrest of the seat while being distributed in two rows separated by a distance corresponding to the width of the spinal column of the driver. In each row, the sensors, with an area of from 16 to 36 $cm^2$, are arranged at equal distances of from 1 to 5 cm from one another. In another embodiment, instead of the two separate sensor rows with sensors distributed over the entire height of the seat at a distance of 1-5 cm, two membrane sensors with a width of from 4 to 10 cm are arranged over the entire seat height with a separation corresponding to the spinal column.

Furthermore, DE 10 2008 049 112 A1 discloses a capacitive textile electrode for measuring body functions and/or vital parameters of persons for vehicle applications, for example in a seat or a bunk, which electrode has a multilayer structure. This comprises two textile layers, each of which has an electrically conductive electrode region, a further textile layer being provided in order to establish a distance between the other two textile layers.

In order to obtain a reliable and stable signal from the previously known sensors or sensor arrangements/sensor arrays for a contactless electrocardiographic measurement of persons in vehicle applications, it is important that the sensors are covered—preferably completely—by the body or the body region to be examined of the subject and that a distance which is as small as possible is ensured between the sensors and the person to be examined. In general, those electrodes that have a distance that is large from e.g. the back of the subject lead to a poor or even unusable signal.

Therefore, in principle, it is possible to attempt to place the sensors e.g. on a sitting or lying surface where a contact which is as good as possible is to be expected with the subject situated on the seat or couch. It is likewise feasible to use more electrodes overall so as to improve the contact between these and the subject. However, any reduction in the electrode surface that may accompany the increase in the number of sensors will probably lead to low sensitivity of the sensors. By way of example, a further option could also consist of using larger electrode surfaces. However, in the case of small or thin subjects, this may lead to whole electrode sections not being covered by the body of the subject and therefore not having a contact with the subject, which may once again leads to an increased susceptibility to faults.

SUMMARY

It is an object of the present invention to provide a sensor, a sensor array and a seat or a couch for the contactless electrocardiographic measurement of persons, preferably in the context of vehicle applications, by means of which reliable statements can be made about the bodily functions and/or vital parameters of the person, i.e. which are able to supply a reliable signal with high signal quality at all times.

The features specified individually in the claims may be combined with one another in any desired technologically meaningful way and disclose further embodiments of the invention. The description, in particular in conjunction with the Figures, characterizes and specifies the invention further.

According to the invention, a sensor for a contactless electrocardiographic measurement of a person comprises at least one electrically conductive, generally planar electrode, which comprises a measurement surface facing the person and a connection surface facing away from the person and lying opposite to the measurement surface. Within the meaning of the present invention, "contactless" should be understood to mean that the measurement surface of the electrode does not come into direct contact with the skin of the subject. By way of example, pieces of clothing may be arranged between the subject and the measurement surface of the electrode.

In accordance with the present invention, an electrical terminal for connecting a measurement apparatus is arranged opposite to the connection surface and is space a distance therefrom.

According to the invention, the connection surface can only be electrically connected to the terminal by means of a pressure applied to the measurement surface of the electrode and acting in the direction of the terminal. That is to say, there is no electrical connection between the electrode and the terminal and hence no signal transmission from the electrode to the measurement apparatus as long as the pressure exerted by the body of the subject on the measurement surface of the electrode in the direction of the terminal is insufficient to establish an electrical connection. Therefore, it is always ensured that the sensor only automatically supplies a signal to the measurement apparatus when there is sufficient pressure between the electrode and the subject by virtue of the latter pressing against the sensor with a body part corresponding to the position of the sensor. The sensor according to the invention does not supply the measurement apparatus with this measurement signal if this sufficient level of pressure does not exist between the electrode and the subject, i.e. if the signal recorded by the measurement surface is likely to be an incorrect and therefore unusable signal. Consequently, reliable statements can be made about the bodily functions and/or vital parameters of the person since the sensor supplies a reliable signal with high signal quality at all times, namely either the usable measurement signal from the electrode or no signal.

In accordance with an advantageous embodiment of the invention, an electrical switching contact is disposed or arranged between the connection surface and the terminal and establishes the electrical connection therebetween. Here, the switching contact is configured so as to establish the electrical connection as a result of the approach of the connection surface of the electrode to the terminal caused by the pressure on the measurement surface of the electrode. To this end, in principle, any conventional switching contact which is able to close the electrical contact between the connection surface of the electrode and the terminal when the connection surface approaches the terminal can be used.

A further advantageous embodiment of the invention, which is particularly simple in terms of its production, provides for the switching contact to comprise a rigid contact pin, the length of which extends in a direction from the connection surface of the electrode to the terminal. Here, the contact pin can be fastened either to the connection surface of the electrode or to the terminal. In this manner, the electrical connection between the connection surface of the electrode and the terminal is established above a predeterminable pressure on the measurement surface of the electrode, depending on the length of the contact pin and the pressure-free distance between the connection surface and the terminal.

An alternative advantageous embodiment of the invention provides for the switching contact to comprise a contact pin, the length of which extends in a direction from the connection surface of the electrode to the terminal, wherein the length can be shortened against a spring force acting on the contact pin. By way of example, the contact pin could be made of at least two contact sleeves arranged within one another, which can be displaced or telescoped relative to one another against the spring force. In other words, the contact pin of the switching contact can be telescoped against the spring force acting on the contact pin even after establishing the electrical connection between the connection surface of the electrode and the terminal. Hence, a further approach of the electrode to the terminal is made possible in accordance with the pressure applied to the measurement surface of the electrode, even if the electrical connection has already been established.

In accordance with a further advantageous embodiment of the invention, a plurality of electrodes is provided on each sensor. Here, the individual electrodes of the sensor can form a larger compound overall electrode surface which is defined by the totality of the individual smaller electrodes and segmented by the individual electrodes. The substantial advantage of this embodiment is that, in this way, a measurement signal is only automatically supplied by those electrode regions of the overall electrode surface on which a sufficiently high pressure is exerted by the subject on the measurement surface of the respective electrode. By contrast, other electrode regions do not supply a measurement signal.

Another advantageous embodiment of the invention provides for the plurality of electrodes in each case to have a measurement surface of approximately 1 $cm^2$ to 16 $cm^2$, preferably approximately 4 $cm^2$, and to be arranged in a matrix-like manner with a distance of less than approximately 1 cm, preferably less than approximately 5 mm, from one another. Accordingly, the overall electrode surface defined by the totality of the individual electrodes can be segmented into relatively small electrode regions which, in the case of sufficient pressure on the respective measurement surfaces of the electrodes, automatically supply a reliable measurement signal. In addition to this matrix-like arrangement, the sensors can also be arranged in any other pattern, e.g. spirally, circularly or stochastically.

In accordance with a further advantageous embodiment of the invention, a compressible intermediate material layer is inserted between the connection surface of the electrode and the terminal. Therefore, the desired pressure required for establishing the electrical connection between the connection surface of the electrode and the terminal can be set exactly on the basis of the compressible intermediate material layer. Furthermore, the intermediate material layer ensures an exactly defined distance between the connection surface of the electrode and the terminal in the pressure-free state.

A sensor array according to the invention comprises at least two sensors of the type according to the invention, as described above. Within the meaning of present invention, a sensor array should be understood to mean any type of arrangement of a plurality of said sensors.

In accordance with an advantageous embodiment of the invention, these sensors are arranged in two spaced-apart rows, wherein, in each row, a plurality of sensors, each with a measurement surface of approximately 1 $cm^2$ to 16 $cm^2$, preferably approximately 4 $cm^2$, are respectively arranged in a matrix-like manner with a distance of less than approximately 1 cm, in particular less than approximately 5 mm, from one another. Accordingly, it is possible to realize a dense arrangement of relative small sensors for the sensor array, which, in the totality thereof, can cover a relatively large area, wherein, in the case of application, only those sensors where a sufficiently large pressure is applied onto the measurement surface thereof, and which therefore have sufficiently good contact with the subject by the sensor array, automatically supply a measurement signal to the respective measurement apparatus.

In accordance with the present invention, a seat or a couch in a vehicle comprises at least one sensor array of the type according to the invention, as described above, for a contactless electrocardiographic measurement of a person situated on the seat or on the couch.

Further features and advantages of the invention emerge from the following description of exemplary embodiments of the invention which are not to be understood as being restrictive and which will be explained in greater detail in the following text, with reference being made to the drawing. In detail in this drawing:

DETAILED DESCRIPTION

As required, detailed embodiments of the present invention are disclosed herein; however, it is to be understood that the disclosed embodiments are merely exemplary of the invention that may be embodied in various and alternative forms. The Figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
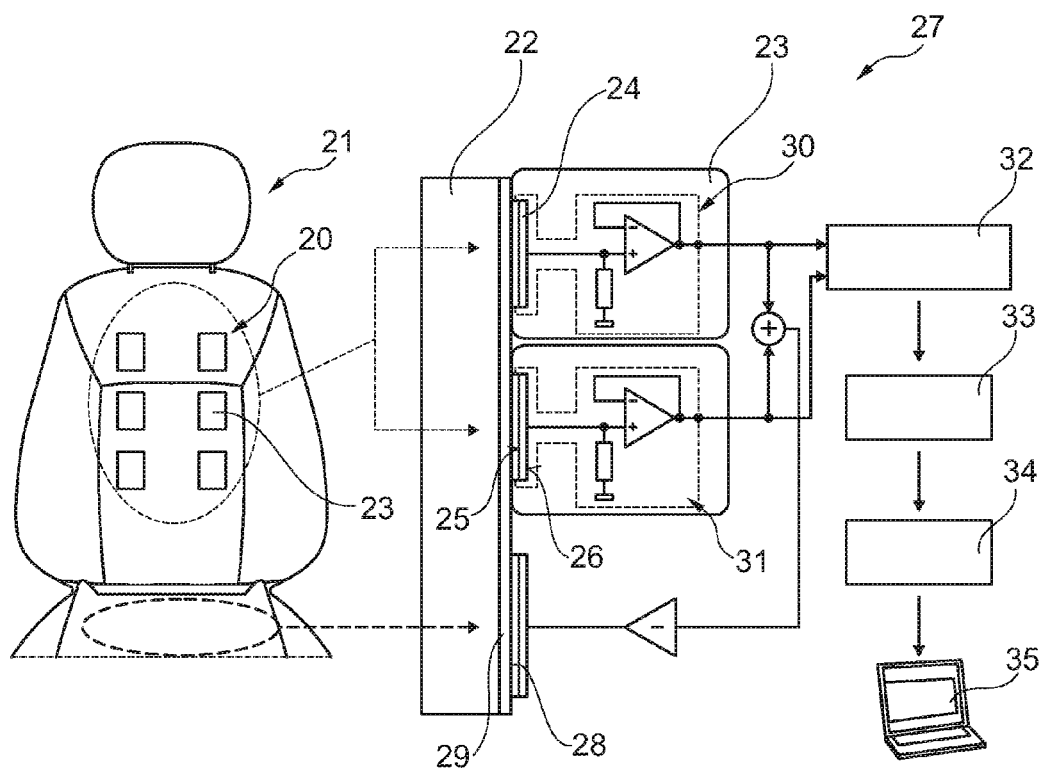
FIG. 1 schematically shows a sensor array and a seat for a vehicle according to the prior art, FIG. 2 schematically shows a cross-sectional view of a sensor according to the invention in accordance with a first embodiment, FIG. 3 schematically shows a cross-sectional view of a sensor according to the invention in accordance with a further embodiment, and FIG. 4 schematically shows a sensor array and a seat for a vehicle according to an embodiment according to the invention.

FIG. 1 schematically represents a sensor array 20 and a seat 21 for a vehicle for contactless electrocardiographic measurement on a person or subject 22, according to the prior art. As can be seen, the sensor array consists of a matrix arrangement of six sensors 23 arranged in a 3×2 matrix in a backrest of a vehicle seat, each of which sensors comprises a flat electrically conductive electrode 24. Another electrode, via which a reference potential is applied to the circuit, is furthermore arranged in the seat surface of the vehicle seat 21.

Each electrode 24 comprises a measurement surface 25 facing the person 22 or their body and a connection surface 26 facing away from the person and lying opposite to the measurement surface 25, for the connection to a measurement apparatus 27. As depicted in FIG. 1, the measurement surface 25 of the individual electrodes 24 does not come into direct contact with the skin of the person 22 to be examined. Rather, an insulation 28 is applied to the measurement surface 25 of each electrode 24 in FIG. 1. Moreover, the clothing 29 worn by the person is furthermore situated between the body of the person 22 to be examined and the measurement surface 25.

The measurement apparatus 27 depicted in FIG. 1 comprises a preamplifier 31 surrounded by shielding 30 for each sensor 23. Furthermore, an instrument amplifier 32 amplifies the measurement signal recorded by the electrodes 24 of the sensors 23, followed by a filter and amplification unit 33 and an A/D converter 34. The digital measurement signal output by the A/D converter 34 can subsequently be processed further in a suitable manner by means of e.g. a digital computer 35.

Within the meaning of the present invention, a measurement apparatus should be understood to mean any apparatus, for example in the form of an electronic circuit, which is suitable for preprocessing a measurement signal recorded by the electrode in any form, for example for amplifying it.

Figure 2:
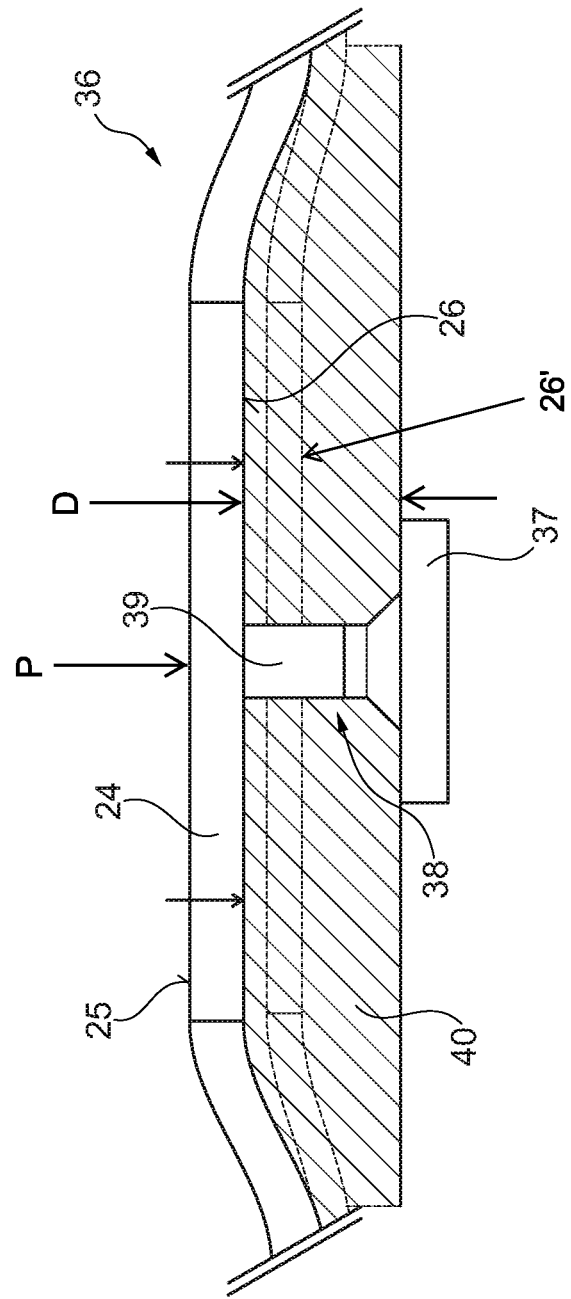

FIG. 2 schematically depicts a cross-sectional view of a sensor 36 for a contactless electrocardiographic measurement of a subject, in accordance with a first embodiment. The sensor 36 depicted in FIG. 2 comprises an electrically conductive, generally flat or planar electrode 24, which comprises a measurement surface 25 facing the subject and a connection surface 26 facing away from the subject and lying opposite to the measurement surface 25. An electrical terminal 37 for connecting the electrode with a measurement apparatus (not depicted in FIG. 2) is arranged opposite to the connection surface 26. When the electrode has little or no pressure exerted on it, it may be said to be in an undeflected condition in which the connection surface 26 is spaced from the terminal 37 by a separation distance D.

When a pressure P of sufficient magnitude is applied to the measurement surface 25 the electrode 24 is moved or deflected relatively toward the terminal 37 to a deflected condition, indicated by the dashed lines in FIG. 2. In the deflected condition, the connection surface 26' of the electrode is relatively closer to the terminal 37, thereby reducing the magnitude of the separation distance D. In the deflected condition indicated by the dashed lines, the connection surface 26 is electrically connected to the terminal 37 by means of a switching contact 38 arranged between the connection surface 26 and the terminal 37.

In the exemplary embodiment depicted in FIG. 2, the switching contact 38 is a substantially rigid contact pin 39, the length of which extends in the direction from the connection surface 26 of the electrode 24 to the terminal 37. When a sufficiently large pressure (as applied by the subject) acts on the measurement surface 25 of the electrode 24 in the direction of the terminal 37, the contact pin 39 moves from a switch-open condition wherein it is spaced apart from the terminal 37 to a switch-closed condition wherein it makes physical contact with both the electrode 24 and the terminal 37 and thereby establishes an electrical connection between the electrode 24 and the terminal 37. A measurement signal recorded by the electrode 24 is then transmitted to a measurement apparatus (not depicted here) electrically connected with the terminal 37. In the case of pressure below the required threshold level being applied to the measurement surface 25 of the electrode 24, the contact pin 39 does not make contact with the terminal 37 so that the switching contact 38 remains in the switch-open condition and measurement signals from the electrode 24 are not transmitted to the measurement apparatus.

In order to be able to exactly define and predetermine the pressure required to place the switching contact 38 in the switch-closed condition, and also the distance between the connection surface 26 and the terminal 37, the exemplary embodiment shown in FIG. 2 includes an appropriately compressible material 40 between the connection surface 26 of the electrode 24 and the terminal 37. In the region of the switching contact 38, the layer 40 has a corresponding hole or recess to receive the switching contact 38.

Figure 3:
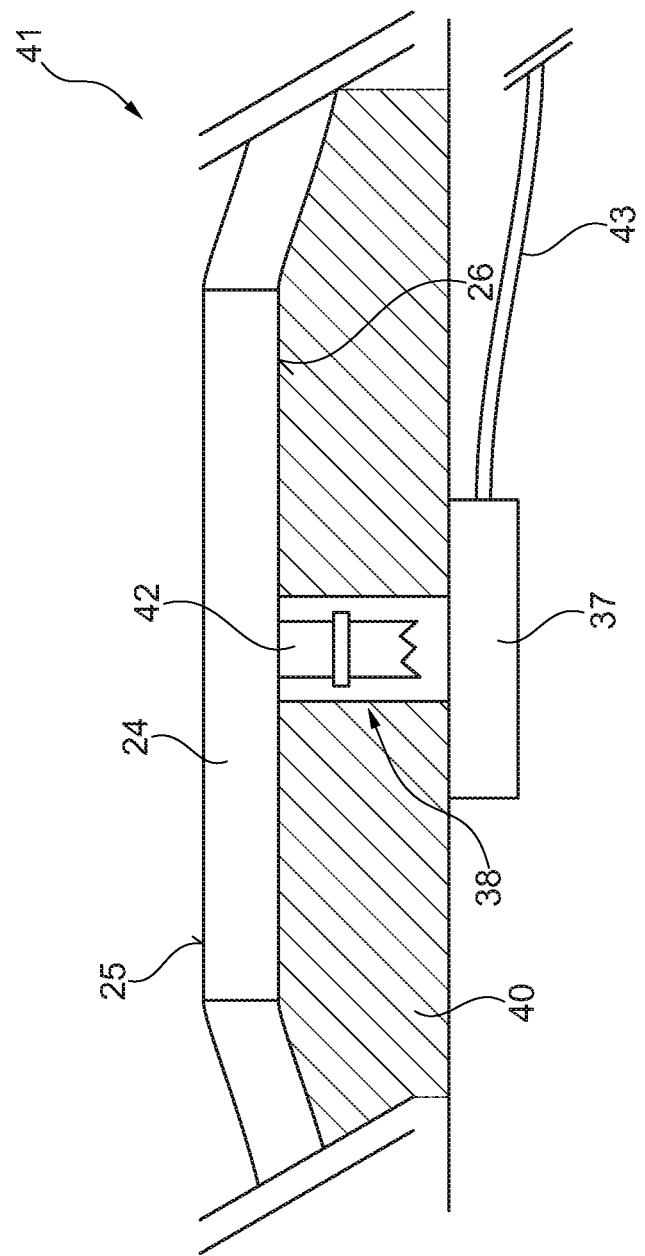

FIG. 3 schematically depicts a cross-sectional view of a sensor 41 in accordance with a further embodiment. The embodiment differs from the embodiment shown in FIG. 2 in the configuration of the switching contact 38. In the embodiment depicted in FIG. 3, the switching contact 38 comprises a contact pin 42, the length of which extends in a direction from the connection surface 26 of the electrode 24 to the terminal 37, wherein the length can be shortened against a spring force acting on the contact pin 42. By way of example, the contact pin can be made of two contact sleeves arranged within one another, which can be displaced or telescoped relative to one another against the spring force. In other words, the contact pin 42 of the switching contact 38 can be telescoped or shortened against the spring force applied to the contact pin 42 even after establishing the electrical connection between the connection surface 26 of the electrode 24 and the terminal 37. Hence, a further shortening of the distance D between the electrode 24 and the terminal 37 is permitted in response to the pressure applied to the measurement surface 25 of the electrode 24, even if the electrical connection has already been established.

Furthermore, a conductive cable 43 for electrically connecting a measurement apparatus (not depicted here) to the terminal 37 is shown in FIG. 3.

Figure 4:
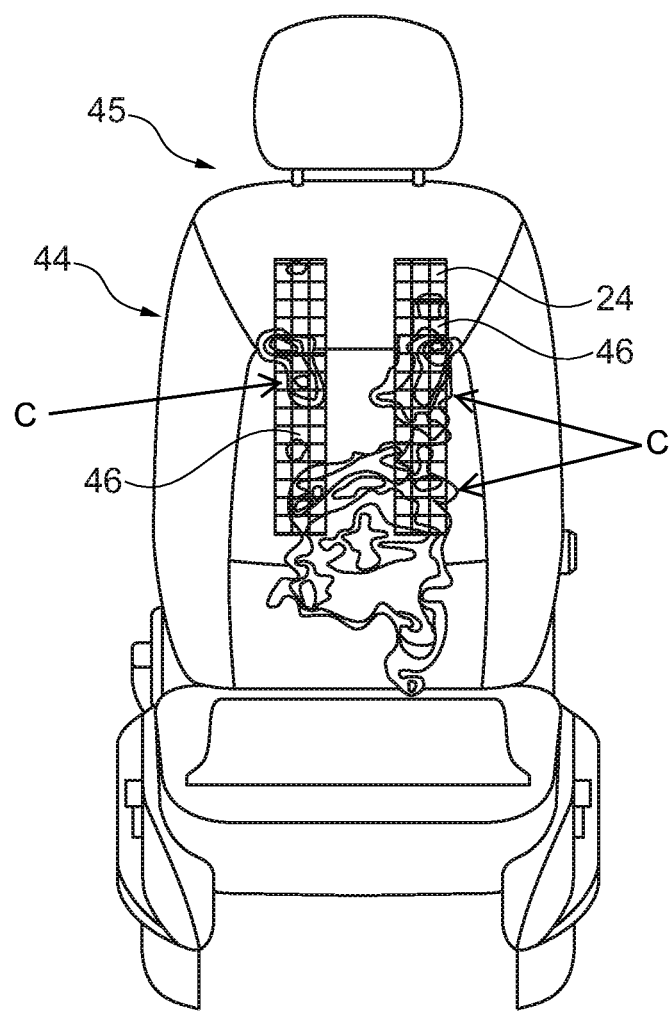

FIG. 4 depicts a sensor array 44 and a seat 45 for a vehicle for contactless electrocardiographic measurement of a subject. The sensor array 44 is arranged in the backrest of the vehicle seat 45 and, in the shown exemplary embodiment, comprises two elongated sensors 46, which are separated laterally from one another and are respectively formed by a plurality of electrodes 24 arranged in a 3×15 matrix. The individual electrodes 24 in each case have a measurement surface of approximately 4 cm² and are arranged in a matrix-like manner with a distance of less than approximately 5 mm from one another.

The multiple sets of contour lines C represent the levels of pressure applied to various areas of the surface of the backrest and the sensor array by the subject (not shown) when seated in the seat 45. FIG. 4 illustrates that, depending on the pressure applied to the electrodes by a subject sitting in the vehicle seat, only some of the plurality of electrodes 24 have sufficient pressure applied to them to cause them to be active, i.e. electrically connected to the respective measurement apparatuses (not depicted here). The remaining electrodes 24 of the respective sensor 46 are accordingly not electrically connected to the associated measurement apparatuses and therefore are inactive. Consequently, only those electrodes 24 on which the amount of pressure exerted by the subject is sufficiently high to establish the electrical connection between the connection surface of the electrode 24 and the terminal 37 are automatically active. As a result of the good contact with the subject, these active electrodes 24 supply a usable measurement signal to the associated measurement apparatus, while the remaining inactive electrodes 24 on which insufficient pressure is applied to achieve electrical continuity between the electrode and the terminal 37 do not supply a measurement signal to the measurement apparatus.

The sensor according to the invention, the sensor array and the seat or the couch were explained in more detail on the basis of a plurality of exemplary embodiments depicted in the Figure. However, the sensor, the sensor array and the seat or couch are not restricted to the embodiments described herein, but rather also comprise further embodiments with the same effect.

In a preferred embodiment, the sensor according to the invention, the sensor array and the seat or the couch are used in a vehicle, in particular in a motor vehicle, for a contactless electrocardiographic measurement of a subject.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A sensor for contactless electrocardiographic measurement of an occupant of a seat, comprising:
   at least one terminal for mounting in a backrest of the seat and for connection with a measurement apparatus;
   a plurality of electrocardiographic electrodes arranged in a matrix for mounting within the backrest to generate a measurement signal of the seat occupant, each electrode having an undeflected condition wherein it is spaced from the at least one terminal by a first distance and movable by pressure applied by the seat occupant to a deflected condition wherein it is spaced from the at least one terminal by a second distance smaller than the first distance; and
   a switching contact between each one of the electrodes and the at least one terminal, each switching contact spaced from at least one of its respective electrode and the terminal when the respective electrode is in the undeflected condition, movement of the respective electrode from the undeflected condition to the deflected condition placing the switching contact in contact with both the electrode and the terminal to conduct the measurement signal from the electrode to the terminal.

2. The sensor of claim 1, wherein at least one of the switching contacts is in contact with its respective electrode when in the undeflected condition and is brought into contact with the terminal by movement of the respective electrode to the deflected condition.

3. The sensor of claim 1, further comprising a compressible material disposed between the plurality of electrodes and the at least one terminal.

4. The sensor of claim 3, wherein at least one of the switching contacts is housed in a recess in the compressible material.

5. The sensor of claim 1, wherein at least one of the switching contacts comprises two parts displaceable relative to one another and urged to an extended condition by a spring force between the two parts, the at least one switching contact in the extended condition having a length less than a distance between the terminal and its respective electrode in the undeflected condition.

6. A motor vehicle seat having a sensor comprising:
   a terminal for connection with a measurement apparatus;
   an electrocardiographic electrode spaced from and movable toward the terminal by pressure applied to the electrode by a seat occupant; and
   a switching contact between the electrode and the terminal and movable between a switch-open condition spaced from the terminal and a switch-closed condition contacting the terminal to conduct a measurement signal from the electrode to the terminal.

7. The sensor of claim 6, further comprising a compressible material disposed between the electrode and the terminal.

8. The sensor of claim 7, wherein the switching contact is housed in a recess in the compressible material.

9. The sensor of claim 6, wherein the switching contact comprises a contact pin comprising two parts displaceable relative to one another and urged to an extended condition by a spring force between the at least two parts, the contact pin in the extended condition having a length less than a distance between the terminal and the electrode prior to pressure being applied to the electrode.

10. The sensor of claim 6, further comprising a compressible material layer disposed between the electrode and the terminal.

11. A seat for a motor vehicle and having a sensor array for contactless electrocardiographic measurement, the sensor array comprising:
   a terminal for connection with a measurement apparatus; and
   an electrode for generating a measurement signal of a subject and having an undeflected condition wherein it is spaced from the terminal by a first distance and movable by pressure applied to a deflected condition wherein it is spaced from the terminal by a second distance smaller than the first distance; and
   a switching contact between the electrode and the terminal and spaced from at least one of the electrode and the terminal when the electrode is in the undeflected condition, movement of the electrode from the undeflected condition to the deflected condition placing the switching contact in contact with both the electrode and the terminal to conduct the measurement signal from the electrode to the terminal.

12. The seat of claim 11, wherein the switching contact is in contact with the electrode when in the undeflected condition and is brought into contact with the terminal by movement of the electrode to the deflected condition.

13. The seat of claim 11, further comprising a compressible material disposed between the electrode and the terminal.

14. The seat of claim 13, wherein the switching contact is housed in a recess in the compressible material.

15. The seat of claim 11, wherein the switching contact comprises two parts displaceable relative to one another and urged to an extended condition by a spring force between the two parts, the switching contact in the extended condition having a length less than a distance between the terminal and the electrode in the undeflected condition.

\* \* \* \* \*